United States Patent [19]

Goralski et al.

[11] Patent Number: 6,090,979
[45] Date of Patent: *Jul. 18, 2000

[54] PROCESS FOR THE PRODUCTION OF VINYL-GABA

[75] Inventors: Christian T. Goralski; John F. Hoops; Kuttanchery Ananthanarayanan Ramanarayanan, all of Midland, Mich.

[73] Assignee: Merrell Pharmaceuticals Inc., Bridgewater, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/912,770

[22] Filed: Aug. 18, 1997

Related U.S. Application Data

[63] Continuation of application No. 08/668,867, Jun. 24, 1996, abandoned, which is a continuation of application No. 08/517,304, Aug. 21, 1995, abandoned, which is a continuation of application No. 08/391,821, Feb. 21, 1995, abandoned, which is a continuation of application No. 08/227,916, Apr. 15, 1994, abandoned, which is a continuation of application No. 08/106,313, Aug. 13, 1993, abandoned, which is a continuation of application No. 07/987,089, Dec. 7, 1992, abandoned, which is a continuation of application No. 07/882,232, May 8, 1992, abandoned, which is a continuation of application No. 07/432,707, Nov. 7, 1989, abandoned.

[51] Int. Cl.[7] .................................................. C07C 227/20
[52] U.S. Cl. .......................................... 562/553; 562/554
[58] Field of Search ...................................... 564/553, 554

[56] References Cited

U.S. PATENT DOCUMENTS

| | | | |
|---|---|---|---|
| 3,974,215 | 8/1976 | Goulay | 562/554 |
| 4,235,778 | 11/1980 | Gittos et al. . | |
| 4,254,284 | 3/1981 | Gittos et al. | 562/574 |
| 4,371,706 | 2/1983 | Edmonds, Jr. et al. | 562/553 |
| 4,529,818 | 7/1985 | Nesheiwat et al. | 562/553 |
| 4,621,145 | 11/1986 | Frieben et al. | 548/543 |

FOREIGN PATENT DOCUMENTS

| | | | |
|---|---|---|---|
| 0116257 | 8/1984 | European Pat. Off. | 562/554 |
| 2607620 | 2/1976 | Germany | 562/554 |
| 56254 | 12/1978 | Israel | 562/554 |
| 56-39050 | 4/1981 | Japan . | |
| 59-62555 | 4/1984 | Japan . | |

*Primary Examiner*—James H. Reamer
*Attorney, Agent, or Firm*—Carolyn D. Moon

[57] ABSTRACT

The present invention is directed to a method for producing vinyl GABA by submitting 5-vinylpyrrolidin-2-one to a basic hydrolysis.

9 Claims, No Drawings

PROCESS FOR THE PRODUCTION OF VINYL-GABA

CROSS-REFERENCE TO RELATED APPLICATION

This is a continuation of application Ser. No. 08/668,867 now abandoned, filed Jun. 24, 1996 which is a continuation of application Ser. No. 08/517,304, filed Aug. 21, 1995 now abandoned; which is a continuation of application Ser. No. 08/391,821, filed Feb. 21, 1995, now abandoned; which is a continuation of application Ser. No. 08/227,916, filed Apr. 15, 1994, now abandoned; which is a continuation of application Ser. No. 08/106,313, filed Aug. 13, 1993, now abandoned; which is a continuation of application Ser. No. 07/987,089, filed Dec. 7, 1992, now abandoned; which is a continuation of application Ser. No. 07/882,232, filed May 8, 1992, now abandoned, which is a continuation of application Ser. No. 07/432,707, filed Nov. 7, 1989, now abandoned—which is herein incorporated by reference.

The present invention is directed to a method for the production of 4-amino-5-hexenoic acid. 4-Amino-5-hexenoic acid is known in the art as an anti-epileptic agent and is described in U.S. Pat. No. 3,960,927. It is also known as vinyl-GABA and is currently available from Merrell Dow Pharmaceuticals, Inc.

U.S. Pat. No. 4,621,145 (hereby incorporated by reference) describes one method for synthesizing this compound. The last step in the reaction sequence is depicted below:

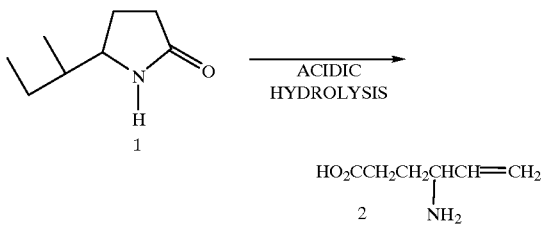

In this reaction 5-vinyl-2-pyrrolidinone (structure 1) is subjected to an acidic hydrolysis thereby producing the desired compound, 4-amino-5-hexenoic acid (structure 2). This acidic hydrolysis is carried out using techniques known in the art. Typically, the 5-vinyl-2-pyrrolidinone is contacted with a strong acid such as hydrochloric acid or trifluoroacetic acid at a temperature above 60° C. in an aqueous solvent system. The 4-amino-5-hexenoic acid is recovered by concentration as is known in the art. The acidic hydrolysis followed by recrystallization produces a yield of 4-amino-5-hexenoic acid of 57–67%. The spent recrystallization liquor can be saved, concentrated, redissolved in ethanol and a second recrystallization can be carried out on this residue which increases the yield of final product by another 10–11%. The yield of 4-amino-5-hexenoic acid which is produced by this process is from 57–67% with one recrystallization and from 70–79% when a second recrystallization is carried out.

It has been discovered that when 5-vinyl-2-pyrrolidinone is subjected to a basic hydrolysis, the yield of purified 4-amino-5-hexenoic acid that is obtained ranges from 80–87% with only one recrystallization being required. Thus the yield of vinyl-GABA is increased by a factor of from 19–52% compared to the acidic hydrolysis in which only one recrystallization is utilized.

This basic hydrolysis can be carried out using techniques known in the art. The 5-vinyl-2-pyrrolidinone is contacted with a molar excess of potassium hydroxide.

Typically from about 1.1 to about 1.5 equivalents are utilized. The basic hydrolysis is carried out at a temperature range of from about 60° C. to 140° C., and more preferably from about 75° C. to 130° C. The reaction is typically carried out for a period of time ranging from about 0.5 hours to about 24 hours.

The basic hydrolysis can either be carried out in water or in a solvent containing water and a lower alkanol such as isopropanol or ethanol. The relative proportions of the lower alkanol and water can vary widely and are not critical to the hydrolysis. It is preferred that the water be present in a minimum quantity of at least 1.5 v/v % in order to expediate the rate of hydrolysis. Carrying out the reaction in water alone allows the hydrolysis to be completed in a shorter period of time.

The resulting 4-amino-5-hexenoic acid can be recovered from the reaction medium using techniques known in the art. Although the relative proportion of lower alkanol to water is not critical to the hydrolysis reaction, it is necessary for a sufficient quantity of the lower alkanol to be present in the reaction zone prior to commencing the recovery of the desired product. The reaction medium should contain from about 60 v/v % to about 90 v/v % of the lower alkanol and more preferably about 85 v/v % of the lower alkanol. If necessary, this quantity of lower alkanol can be added to the reaction medium after the hydrolysis is completed. Once a sufficient quantity of the lower alkanol is present in the reaction medium, the 4-amino-5-hexenoic acid can be recovered by adding approximately one equivalent of an acid such as glacial acetic acid or propionic acid to the reaction. The 4-amino-5-hexenoic acid will be converted to its free base and will precipitate from solution. The precipitate is then recovered by filtration, washed and dried as is known in the art. The 4-amino-5-hexenoic acid can then be purified by recrystallization from a solvent system such as isopropanol/water.

The following Examples are being presented in order to exemplify the invention but they should not be construed as limiting the scope of the invention in any manner.

EXAMPLE I

Basic Hydrolysis of 5-Vinyl-2-pyrrolidinone with Potassium Hydroxide in Isopropanol/Water.

A 2-L, three-neck flask equipped with a magnetic stirrer, a thermowell, and a nitrogen bubbler was charged with 85.0 g (0.765 mol) of 5-vinyl-2-pyrrolidinone, 75 mL of deionized water, and 900 mL of isopropanol. To this was added 75.0 g (1.136 mol) of 85% potassium hydroxide, and the mixture heated to reflux. After 24 hours, the reflux was stopped and the reaction cooled to ambient temperature. The reaction was treated with 69.0 g (1.149 mol) of glacial acetic acid. The resulting solution was seeded with vinyl GABA and a heavy slurry of white solid formed. The slurry was cooled to ambient temperature and then stirred with ice-bath cooling for 2 hours. The solid was separated by filtration, washed with two 100 mL portions of ice-cold isopropanol, air dried, and vacuum dried at 35–40° C. to give 92.22 g (93% yield) of crude vinyl GABA as a white, crystalline solid.

An 84.30 g sample of this crude vinyl GABA was mixed with 120 mL of deionized water and the slurry heated until a cloudy solution formed. The solution was filtered through a medium (M) glass frit and washed through with 23 mL of boiling water followed by 20 mL of boiling water. The filtrate was heated to near reflux and 756 mL of isopropanol was slowly added. A slurry of white solid formed. The slurry was cooled to ambient temperature and then stirred with ice-bath cooling for 2 hours. The solid was separated by filtration, washed with two 50 mL portions of ice-cold isopropanol, air dried, and vacuum dried at 35–40° C. to give 78.68 g of vinyl GABA as a white, crystalline solid, mp 178.5–179° C. The final yield was 87%.

EXAMPLE II
Basic Hydrolysis of 5-Vinyl-2-pyrrolidinone with Potassium Hydroxide in Isopropanol/Water. Preparation of Vinyl GABA.

A 2-L, three-neck flask equipped with a magnetic stirrer, a thermowell, two glass stoppers, and a reflux condenser fitted with a nitrogen bubbler was charged with 85.0 g (0.765 mol) of 5-vinyl-2-pyrrolidinone, 75 mL of deionized water, and 900 mL of isopropanol. To this mixture, 75.0 g (1.136 mol) of 85% potassium hydroxide was added and the mixture heated to reflux. After 24 hours, the reaction was cooled to approximately 50° C. and 69.0 g (1.149 mol) of glacial acetic acid was added. The slurry of white solid which formed was cooled to ambient temperature and then stirred with ice-bath cooling for 2 hours. The solid was separated by filtration and washed with two 100 mL portions of ice-cold isopropanol. The solid was air dried and then vacuum dried to give 88.19 g (89% yield) of crude vinyl GABA as a white, crystalline solid.

An 83.10 g sample of this vinyl GABA was mixed with 120 mL of deionized water and the mixture heated to reflux to give a cloudy solution. The solution was filtered through filter paper into a 2-L, single-neck flask equipped with a magnetic stirrer. The beaker and the filter were rinsed with two 25 mL portions of hot water and the filtrate heated to reflux. To the hot filtrate was added 750 mL of isopropanol. The solution was cooled to ambient temperature to give a slurry of white solid. The slurry was stirred for 2 hours with ice-bath cooling. The solid was separated by filtration, washed with two 100 mL portions of ice-cold isopropanol, air dried, and vacuum dried at 40° C. to give 75.08 g of vinyl GABA as a white, crystalline solid, mp 179–180° C. The final yield was 81%.

EXAMPLE III
Basic Hydrolysis of 5-Vinyl-2-pyrrolidinone with Potassium Hydroxide in Ethanol/Water. Preparation of Vinyl GABA.

A 500-mL, single-neck flask equipped with a magnetic stirrer and a reflux condenser fitted with a nitrogen bubbler was charged with 27.07 g (0.244 mol) of 5-vinyl-2-pyrrolidinone, 25 mL of deionized water, 300 mL of ethanol, and 24.10 g (0.366 mol) of 85% potassium hydroxide. The mixture was heated to reflux and held there for 24 hours. The reaction was cooled to ambient temperature and 22.17 g (0.369 mol) of glacial acetic acid was added. A white solid rapidly began to crystallize, and the slurry was stirred at room temperature over night. The slurry was cooled with an ice bath. The solid was separated by filtration, washed with two 50 mL portions of cold ethanol, air dried, and vacuum dried at 35° C. to give 24.73 g (78% yield) of crude vinyl GABA as a white, crystalline solid.

EXAMPLE IV
Hydrolysis of 5-Vinyl-2-pyrrolidinone with Potassium Hydroxide in Water.

A 500-ml, single-neck flask equipped with a magnetic stirrer and a reflux condenser fitted with a nitrogen bubbler was charged with 85.0 g (0.765 mol) of 5-vinyl-2-pyrrolidinone, 75 mL of deionized water, and 53.0 g (0.874 mol) of 87% potassium hydroxide. The resulting mixture was heated to reflux and held there for 1.0 h. The reaction mixture was cooled to ambient temperature and homogeneous orange solution resulted. The solution was diluted with 700 ml of isopropanol and 52.50 g (0.874 mol) of glacial acetic acid was added. A slurry of white solid formed. The slurry was cooled to 0–5° C. and stirred at that temperature for 2 h. The solid was separated by filtration, washed with two 50-mL portions of cold isopropanol, air dried, and vacuum dried at 55° C. to give 89.72 g (90.8% yield) of vinyl GABA as a white solid. The vinyl GABA was mixed with 130 mL of deionized water and the mixture heated to reflux to give a hazy solution. The solution was filtered through a coarse (C) glass frit. The frit was washed with 20 mL of refluxing deionized water. The filtrate was diluted with 750 ml of isopropanol and a slurry of white solid formed. The slurry was cooled to 0–5° C. and stirred at that temperature for 2 hours. The solid was separated by filtration, washed with two 50-ml portions of cold isopropanol, air dried, and vacuum dried at 55° C. to give 85.5 g of vinyl GABA as a white, crystalline solid, mp 179–180° C.

EXAMPLE V (COMPARATIVE EXAMPLE)
Acidic Hydrolysis of 5-Vinyl-2-pyrrolidinone to Vinyl GABA.

A 1-L, three-neck flask equipped with a mechanical stirrer, a thermometer, and a reflux condenser fitted with a nitrogen bubbler was charged with 50.00 g (0.45 mol) of 5-vinyl-2-pyrrolidinone, 300 ml of deionized water, and 50 mL of concentrated hydrochloric acid. The reaction mixture was heated to 95° C. during 30 min. and stirred at that temperature for 5 h. The reaction mixture was concentrated in vacuo (85° C./10–15 mm) to afford 83.8 g of red-orange oil. This material was transferred, along with 500 mL of ethanol, to a 1-L, three-neck flask equipped with a mechanical stirrer. To the rapidly stirred solution, 70 mL (50.82 g, 0.50 mol) of triethylamine was added in portions over 30 min. The reaction temperature was between 32° C. and 34° C. and the final pH was approximately 7 to 8. The precipitated product was collected by filtration, washed with two 50-mL portions of ethanol, and air dried to give 51.28 g of crude vinyl GABA as a white-pink solid. The crude vinyl GABA was dissolved in 70 mL of deionized water and 2.0 g of Darco activated carbon was added. The resulting mixture was heated at 90° C. for 30 min. with occasional swirling. The mixture was filtered hot through a Celite pad. The filtrate was transferred to a 1-L flask and diluted with 420 mL of ethanol. The resulting solution was cooled with an ice bath and stirred for 3 h. The solid was collected by filtration, washed with two 50 mL portions of ethanol, air dried, and vacuum dried for 24 h at 36–38° C. and 60–70 mm to give 32.00 g (57% yield) of vinyl GABA as a white solid, mp 174–174.5° C.

What is claimed is:

1. In a process for producing 4-amino-5-hexenoic acid by subjecting 5-vinyl-2-pyrrolidone to a hydrolysis reaction wherein the improvement comprises subjecting the 5-vinyl-2-pyrrolidone to a basic hydrolysis with potassium hydroxide in water.

2. A process for producing 4-amino-5-hexenoic acid comprising:
   a) subjecting 5-vinyl-2-pyrrolidinone to a basic hydrolysis with potassium hydroxide in water;
   b) precipitating the resulting 4-amino-5-hexenoic acid from the reaction mixture, by treating the reaction mixture with a lower alkanol and either acetic acid or propionic acid, and;
   c) recovering the precipitated 4-amino-5-hexenoic acid.

3. A process according to claim 1 in which the order of addition of the lower akanol is modified by adding said lower alkanol at the initiation of or during said basic hydrolysis reaction and not at the initiation of or during said precipitation.

4. A process according to claim 3 wherein said potassium hydroxide is present in the amount of from 1.1 to 1.5 equivalents.

5. A process according to claim 4 wherein said hydrolysis is carried out in a solvent containing a lower alkanol and at least 1.5 v/v % of water.

6. A process according to claim 5 wherein said lower alkanol is isopropanol.

7. A process according to claim 4 wherein said resulting 4-amino-5-hexenoic acid is recovered and purified.

8. A process according to claim 2 in which the hydrolysis is carried out at a temperature range of from 75° to 130° C. for a period of time ranging from 0.5–24 hours.

9. A process according to claim 8 wherein said resulting 4-amino-5-hexenoic acid is recovered and purified.

\* \* \* \* \*